United States Patent
Fukushima et al.

(10) Patent No.: US 8,343,333 B2
(45) Date of Patent: Jan. 1, 2013

(54) ELECTRODE SUBSTRATE, DETECTION DEVICE EQUIPPED WITH ELECTRODE SUBSTRATE, DETECTION DEVICE KIT AND DETECTION METHOD USING THE KIT

(75) Inventors: Hitoshi Fukushima, Suwa (JP); Hiroshi Takiguchi, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 1493 days.

(21) Appl. No.: 11/360,699

(22) Filed: Feb. 24, 2006

(65) Prior Publication Data
US 2006/0196779 A1    Sep. 7, 2006

(30) Foreign Application Priority Data
Mar. 7, 2005   (JP) ................. 2005-063123

(51) Int. Cl.
*G01N 27/327*  (2006.01)
(52) U.S. Cl. .............. 205/792; 204/403.06; 435/177
(58) Field of Classification Search ............. 204/403.01–403.15; 205/777.5, 205/778, 792; 600/345–348; 422/50–99, 422/68.1–98; 435/4–40.52, 176, 177, 180, 435/181; 436/62–71, 500–548
See application file for complete search history.

(56) References Cited

U.S. PATENT DOCUMENTS

| | | | | |
|---|---|---|---|---|
| 4,100,029 A | * | 7/1978 | Prosperi et al. | 435/182 |
| 4,321,123 A | * | 3/1982 | Nakamura et al. | 204/403.14 |
| 5,202,261 A | * | 4/1993 | Musho et al. | 204/403.09 |
| 5,229,282 A | * | 7/1993 | Yoshioka et al. | 435/177 |
| 5,443,701 A | * | 8/1995 | Willner et al. | 205/777.5 |
| 5,445,934 A | | 8/1995 | Fodor et al. | |
| 5,637,201 A | | 6/1997 | Raguse et al. | |
| 6,214,205 B1 | | 4/2001 | Willner et al. | |
| 6,280,590 B1 | | 8/2001 | Cheng et al. | |
| 6,355,420 B1 | * | 3/2002 | Chan | 435/6 |
| 6,479,240 B1 | | 11/2002 | Kayyem et al. | |
| 7,172,897 B2 | | 2/2007 | Blackburn et al. | |
| 2003/0070548 A1 | * | 4/2003 | Clausen | 96/4 |

FOREIGN PATENT DOCUMENTS

| | | |
|---|---|---|
| GB | 2313912 A | 12/1997 |
| JP | A 6-78791 | 3/1994 |
| JP | A 6-90754 | 4/1994 |
| JP | 2004-515231 A | 5/2004 |
| WO | WO 02/43864 A2 | 6/2002 |
| WO | WO 03/051506 A1 | 6/2003 |

OTHER PUBLICATIONS

Piro et al. Journal of Electroanalytical Chemistry, 2001, 512(1-2) 101-109.*
Khan, S. "Models of Electron-Transfer Reactions at a Biological-Membrane-Covered Electrode-Solution Interface." J. Phys. Chem.., 1998, vol. 92, pp. 2541-2546.
Fedurco, M. "Redox Reactions of Heme-Containing Metalloproteins: Dynamic Effects of Self-Assembled Monolayers on Thermodynamics and Kinetics of Cytochrome *c* Electron-Transfer Reactions." Coordination Chemistry Reviews, 2000, vol. 209, pp. 263-331.

* cited by examiner

*Primary Examiner* — Alex Noguerola
*Assistant Examiner* — Gurpreet Kaur
(74) *Attorney, Agent, or Firm* — Oliff & Berridge, PLC

(57) ABSTRACT

An electrode substrate including an electrode and a membrane provided on the electrode and having a thickness with which a carrier is exchanged between the electrode and the membrane.

12 Claims, 5 Drawing Sheets

ELECTRODE SUBSTRATE, DETECTION DEVICE EQUIPPED WITH ELECTRODE SUBSTRATE, DETECTION DEVICE KIT AND DETECTION METHOD USING THE KIT

BACKGROUND OF THE INVENTION

1. Technical Field

The present invention relates to an electrode substrate for detecting a subject material in various fields and a detection device equipped with the substrate. More particularly, the invention relates to an electrode substrate that detects an exchange of carriers such as electron between the subject material and the electrode substrate, and relates to the detection device and the like equipped with the substrate.

2. Related Art

Since the mapping of the human genome has finished, a detection device that can efficiently and precisely identify biomolecules such as deoxyribonucleic acid (DNA), protein and antibody molecules has been playing an important role. The detection device can detect the information about the structure, function, weight, electric property and optical property of the sample containing the biomolecules and can transmit the information as data. As such detection device, for example, there is a biochip that can analyze a mass of samples in a short period of time. U.S. Pat. No. 5,445,934 is a first example of related art, and U.S. Pat. No. 6,280,590 is a second example of related art. The first example describes that the biochip adopts a method to measure fluorescence intensity for detecting DNA hybridization. The second example describes that the biochip adopts a method to measure a difference in DNA displacement that varies depending on the applied-electric field. Monitoring the intensity variation of the fluorescent reaction is becoming a mainstream method in this field as described in the examples.

Moreover, there has been an increasing demand for a sensor or a microchip that can detect biological reactions related to the biomolecules such as enzyme, DNA and antibody in real time and in vitro rather than in vivo. After the human genome project, a function analysis of DNA strand has becoming the mainstream of the study. Especially, the function analysis of the proteins including the enzyme composed of the DNA strand and the antibody, and optimization of a target used in the drug discovery according to the result of the analysis are becoming a mainstream trend. In order to efficiently conduct the analysis, in other words, for a high throughput, it is important to utilize a DNA chip and a protein chip. The key of the chip technology is a capability of a biointerface (hereinafter called "BI") that serves as a detection mechanism between the reaction of the biomolecules and a detection method (light detection such as fluorescence, electrochemical detection, detection of small weight and the like).

The BI needs to be capable of sorting out the useful information of the biological reactions, amplifying the useful information parameter, and converting or transferring the information parameter to a detection parameter.

Following the practical application of the electrochemical detection device utilizing an enzyme molecule which is a representative example of the detection device having the BI function, a great demand for such detection devices is expected in the future. To be more specific, there is a detection device for monitoring blood sugar levels of diabetic patients. JP-A-6-78791, JP-A-6-90754 and JP-T-8-78791 are third-fifth examples of related art. As described in the third-fifth examples, enzyme molecules of glucose-oxidase or glucose-dehydrogenase that oxidizes glucose molecule to be gluconic acid are immobilized on an electrode substrate. Glucose contained in the blood is oxidized so as to be the gluconic acid in an enzyme molecular film on the substrate, generating an oxidation current. Accordingly, the blood sugar levels can be measured in real time by detecting the generated oxidation current that is captured with the electrode.

Generally, in the detection device for monitoring the blood sugar levels, a solution in which the biomolecule such as enzyme molecule is dispersed in a water-soluble polymer such as cellulose is applied on the electrode by a spin-coat method and the like, and a mixed dispersion film is formed. Alternatively, the biomolecule can be immobilized or semi-immobilized (loose retention by noncovalent binding) on the surface of the electrode substrate by utilizing a self-assembled monolayer (hereinafter called "SAM"). The blood sugar levels can be monitored by detecting a pseudo-biological reaction occurred on the solid surface. This biomolecule immobilization method utilizing the SAM is rapidly becoming the mainstream in this field so far.

However, some problems are pointed out in the above-described method of immobilizing the SAM on the surface of the electrode substrate as follows: (1) It is difficult to control the interaction between the surface of the electrode substrate and the biomolecule since the SAM is a monolayer film. For example, if the biomolecule contacts with a metal surface, the biomolecule, especially the enzyme and the like, could be denatured and the activity of the enzyme could be lost. (2) It is difficult to control the nonspecific adsorption between the surface of the electrode substrate and the biomolecule. For example, the biomolecule could be absorbed to the surface of the electrode substrate with an electrostatic force and van der Waals' force. (3) It is difficult to tell that the device is monitoring either the oxidation current generated in the enzyme reaction or a leakage current because the monolayer film is too thin. (4) With the hitherto known SAM, it is difficult to detect an oxidation-reduction current of the enzyme and the like generated in the electrode substrate under the film because the SAM has a high insulation quality. Otherwise, it is difficult to form a selectively permeable membrane because the film thickness and the density of the SAM are so small that the leakage current tends to be generated.

SUMMARY

An advantage of the invention is to provide an electrode substrate and the like on which a membrane through which only electrons can be selectively transported without adhering the biomolecule onto the electrode substrate is provided.

The inventor made researches to seek the membrane through which only carriers such as electrons and holes can be selectively transported without absorbing the biomolecule to the surface of the electrode substrate, and found out that such membrane can be obtained when the membrane has a specific thickness and provided on the electrode substrate. Based on this finding, the invention is achieved.

According to a first aspect of the invention, an electrode substrate including an electrode and a membrane provided on the electrode and having a thickness with which a carrier is exchanged between the electrode and the membrane. In this way, it is possible to realize the electrode substrate through which only carriers such as electrons and holes can be selectively transported without adhering the biomolecule and the like onto the electrode substrate.

In this case, it is preferable that the thickness is 10-80 Å. With this thickness, the detection of the leakage current can be avoided. At the same time, it is possible to selectively detect, for example, the oxidation current or the reduction current produced as a result of the reaction with the biomolecule.

According to a second aspect of the invention, an electrode substrate includes an electrode and a membrane made of a material that includes an oxygen atom and provided on the electrode. In this way, it is possible to provide the electrode substrate through which only carriers such as electrons and holes can be selectively transported.

In this case, it is preferable that the membrane is made of the material that has the oxygen atom in its main chain. The carriers can be selectively transported through the membrane by providing the oxygen atom in the main chain. More specifically, a material containing a branched macromolecule such as a dendrimer having the oxygen atom in its main chain can be used to form the membrane.

It is also preferable that the material includes a chemical compound having a straight-chain structure and an oxygen atom in the straight-chain structure. The carriers are more selectively transported by providing the oxygen atom in the straight-chain structure.

Moreover, it is preferable that the membrane is a monolayer including a chemical compound selected from the group consisting of a compound having a group represented by —$CH_2$—, a compound having a group represented by —$CH_2CH_2O$—, a compound having groups represented by —$CH_2$— and —$CH_2CH_2O$— and a compound having a group represented by the following formula (1).

Formula 1

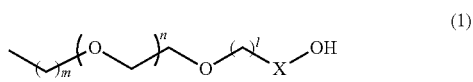

(1)

(where m, n and l are positive integers more than 0, and X indicates a methylene group or a carbonyl group.)

By providing the monolayer having such structure on the electrode substrate, the biomolecule and the like will not adhere to the electrode substrate and only the carriers are selectively transported.

It is preferable that the membrane includes a functional group and a mediator or a biomolecule through the functional group. The effective carrier exchange becomes possible by providing the mediator or the biomolecule to the monolayer.

It is also preferable that the electrode and the membrane are bonded through a sulfur atom or an oxygen atom. With such derivative, the membrane can be firmly fixed to the electrode substrate while having an ordered structure.

Furthermore, it is preferable that wherein the biomolecule is selected from the group consisting of nucleic acid, protein, enzyme and antibody. By using these molecules, it is possible to detect the carriers due to the exchange of the electrons based on the interaction with the subject material, in other words, the current.

According to a third aspect of the invention, a detection device includes the above-described electrode substrate, a counter electrode opposing the electrode substrate and a reference electrode. With such detection device, it is possible to detect the subject material in vitro.

In this case, it is preferable that the detection device further includes a detection circuit individually coupled to the electrode substrate, the counter electrode and the reference electrode. With such detection device, it is possible to detect the generated current.

According to a forth aspect of the invention, a detection kit for detecting a subject material includes the above-mentioned detection device and a biomolecule or a mediator reacting with the subject material. With this kit, it is possible to determine the presence or absence of the subject material. In this case, the biomolecule is preferably enzyme. When the enzyme is used, an antigen-antibody reaction and an oxidation-reduction reaction are occurred with the molecules exiting in the sample. The carriers, more specifically, the electrons produced as a result of the reaction can be detected at the electrode substrate as the oxidation current or the reduction current.

In this case, it is preferable that the detection kit further includes a buffer solution. By using the buffer solution, it is possible to control the pH of the sample containing the subject material, and this provides the reproducibility of the detection.

According to a fifth aspect of the invention, a method of detecting a subject material in a sample includes a step of providing the above-described detection kit and a step of contacting the sample with the kit. In this way, it is possible to simply detect a specific subject material in the sample.

In this case, it is preferable that the method further includes a step of measuring a current value in the presence of the subject material. Based on the result of the measured current value, the presence or absence of the subject material in the sample can be determined. Moreover, it is possible to decide the concentration of the subject material by comparing the measured current value with a current value measured under the absence of the subject material.

BRIEF DESCRIPTION OF THE DRAWINGS

The invention will be described with reference to the accompanying drawings, wherein like numbers reference like elements.

DESCRIPTION OF THE EMBODIMENTS

The following description will be given by way of example only and it will be appreciated by a person skilled in the art that modifications can be made without departing from the scope of the invention.

Figure 1:
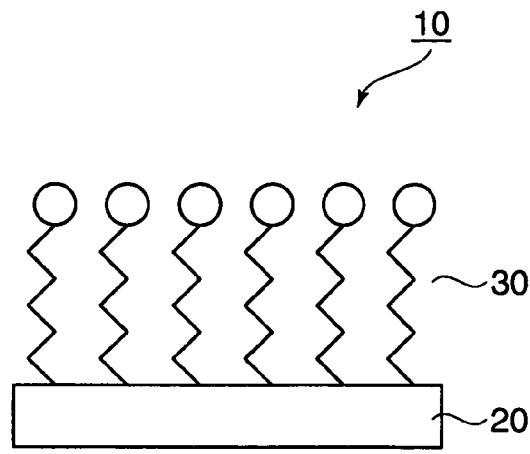
FIG. 1 is a schematic sectional view of an electrode substrate for detecting current according to an embodiment of the invention.

FIG. 1 is a schematic sectional view of an electrode substrate 10 according to an embodiment of the invention. The electrode substrate 10 according to an embodiment of the invention has an electrode 20 and a membrane 30 provided on the electrode 20. The membrane 30 has a thickness with which carriers such as electrons and holes can be exchanged between the electrode 20 and the membrane 30. Material to form the electrode 20 used in the embodiment is not particularly limited. For example, carbon, gold, silver, platinum, copper and the like can be used. Though the electrode shown in FIG. 1 has a plate shape, the form of the electrode is not especially limited. For example, it may have a column shape such as a pin.

The membrane 30 used in the embodiment of the invention prevents a subject material or the biomolecules reacting with the subject material from adhering to the surface of the electrode 20 when the detection of the subject material is carried out by using the electrode substrate 10 according to the embodiment. The membrane 30 is a film through which only the carriers such as the electrons and the holes can be selectively transported. The biomolecule used here is, for example, nucleic acid such as DNA and ribonucleic acid (RNA) and the protein such as the enzyme and the antibody. A film thickness of the membrane 30 according to the embodiment is preferably 10-80 Å, more particularly 10-50 Å, and especially 10-30 Å in consideration of the prevention of the biomolecule's adhesion to the surface and the selective permeation of the electrons. However, the thickness of the membrane can be adequately decided depending on the properties of the material composing the membrane and an intended purpose of the membrane.

According to the other embodiment of the invention, the membrane 30 used on the electrode substrate 10 according to the invention is made of a material containing an oxygen atom. More specifically, the material has the oxygen atom in its main chain. As a specific example of the material having the oxygen atom in its main chain, there is a branched macromolecule such as a dendrimer. The material includes chemical compounds having a straight-chain structure and the oxygen atom may be included in the straight-chain structure.

A group composing the membrane 30 used in the embodiment is not particularly limited as long as the membrane can have a predetermined thickness as described above. For example, there is a monolayer that includes a compound having a group represented by "—CH$_2$—", a compound having a group represented by "—CH$_2$CH$_2$O—", a compound having the groups represented by "—CH$_2$—" and "—CH$_2$CH$_2$O—", and a compound having a group represented by the following formula (1).

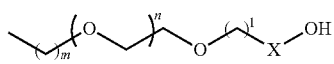

(where m, n and l are positive integers more than 0, and X indicates a methylene group or a carbonyl group.)

A functional molecule forming the membrane 30 according to the embodiment of the invention is not especially limited. For example, as the functional molecule, molecules including the compound having a group represented by "—CH$_2$—", the compound having a group represented by "—CH$_2$CH$_2$O—", the compound having the groups represented by "—CH$_2$—" and "—CH$_2$CH$_2$O—" and the compound having a group represented by the following formula (1) can be named.

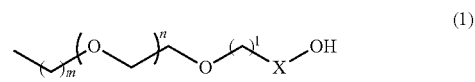

(where m, n and l are positive integers more than 0, and X indicates a methylene group or a carbonyl group.) Such functional molecule has a functional group that can be bonded to the electrode surface in order to form the membrane. The functional molecule is selected according to a relation with the type of the electrode and the like. As the functional group of the functional molecule according to the embodiment which is bondable to the electrode, chalcogen atoms such as a sulfur atom, an oxygen atom and the like can be named. Giving a specific example of the compound having the sulfur atom that works for the bonding, there is a compound including a thiol group (—SH), a disulfide group (—SS) and the like. As for the compound having the oxygen atom that works for the bonding, a compound including a silyl group (—Si) and the like can be named.

Figure 2A:
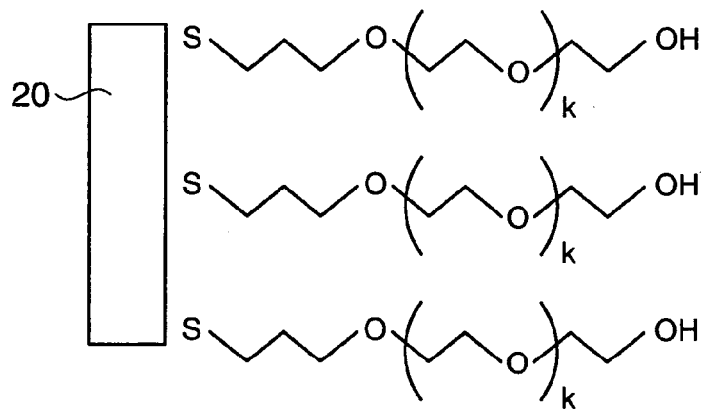
FIGS. 2A and 2B are schematic sectional views of the electrode substrate according to an embodiment of the invention.
Figure 2B:
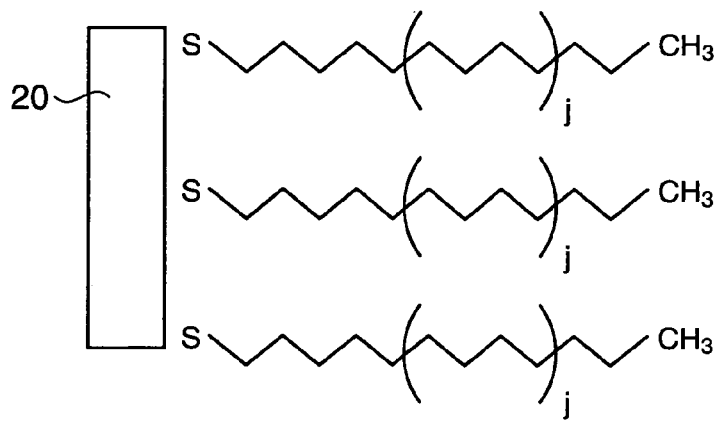

FIG. 2 is a schematic sectional view of the electrode substrate according to an embodiment of the invention. The membrane 30 shown in FIG. 2A is made by using a functional molecule having polyethyleneglycol that has the thiol group on its end. The membrane 30 shown in FIG. 2B is made by using a functional molecule having polyethylene that has the thiol group on its end. Here, the numbers "k" and "j" shown in FIG. 2 are integers that lie within the range of 20-30. Such membrane can be formed on the electrode by using mPEG thiol or PEG thiol propionic acid manufactured by Polypure. These functional molecules are represented by the following formula (2) and formula (3).

Formula (2) Formula (3)

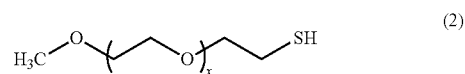

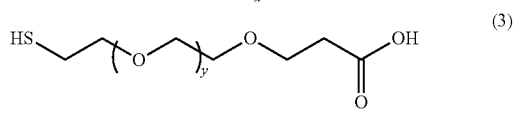

where x and y are integers.

A method of forming the membrane 30 in the embodiment of the invention is described. A method of forming the electrodes shown in FIG. 2A and FIG. 2B is not limited to the hereinafter described method. However, the membrane can be formed on the electrode by immersing the electrode in a solution containing the above-mentioned functional molecule.

Figure 3:
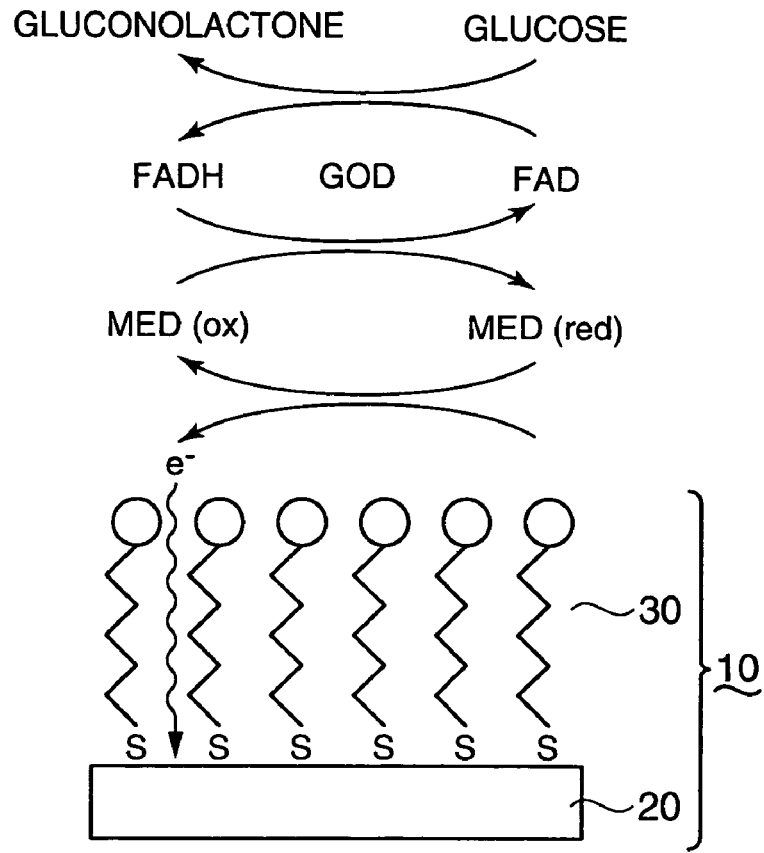
FIG. 3 is a schematic view showing a frame format of glucose concentration measurement using the electrode substrate according to the embodiment of the invention.

Next, an application example of the electrode substrate according to the embodiment of the invention is described. According to an embodiment of the invention, the electrode substrate can be applied to measurement of glucose concentration (blood sugar levels) of diabetic patients. FIG. 3 is a schematic view showing a frame format of glucose concentration measurement using the electrode substrate according to the embodiment of the invention. In this embodiment shown in FIG. 3, the glucose is detected as the subject material. As shown in FIG. 3, the glucose in the blood sample is oxidized to be gluconolactone through the action of glucose oxidase (hereinafter called GOD) on the electrode 10 while flavin adenine dinucleotide (FAD) that is placed in the active center of the enzyme GOD is reduced to FADH (reduced body). The electrons stored in the FADH reach to the electrode 10 according to the embodiment through a mediator (hereinafter called MED). At this point, the electrons selectively penetrate through the membrane provided on the electrode substrate 10 according to the embodiment and move to the electrode substrate 10. Accordingly, the movement of the electrons is detected as an oxidation current. Therefore, the amount of the glucose which is the subject material in the sample can be found out from the detected value of the current. The measurement of the current can be carried out by cyclic voltammetry, differential pulse voltammetry and the like.

When the thickness of the membrane 30 formed on the electrode substrate 10 according to the embodiment of the invention is larger than a specific thickness, the membrane becomes a barrier for the electrons that move towards the electrode and the measurement of the oxidation current becomes impossible. On the other hand, when the thickness of the membrane is smaller than the specific thickness, the biomolecule and the like sticks to the surface of the electrode and the biomolecule of the enzyme and the like could be denatured.

In the above-described case of the glucose concentration measurement, the mediator used in the embodiment is not especially limited. For example, ferrocene, ferrocene derivative and the like can be used. Pyroquinoline quinone, nicotinamide adenine dinucleotide and the like may be put together as a reaction coenzyme.

According to the other embodiment of the invention, the GOD and the MED may be bonded to the membrane through the functional group in the end chain of the membrane on the electrode substrate. More specifically, when the molecule having the group represented by "—$CH_2CH_2O$—" and a hydroxyl group (—OH) on its end is used as a monomolecule forming the membrane, the MED and the like can be coupled through the hydroxyl group. Furthermore, a maleimide group or N-hydroxysuccinimide group can be introduced by utilizing the reactivity of the hydroxyl group. The biomolecule can be directly introduced into the membrane 30 by making reaction between the group and a reactive amino group and a thiol group that exists in the surface of the enzyme.

The electrode substrate 10 according to the embodiment of the invention can also be used for the detection of reactive oxygen species. Here, the reactive oxygen species includes superoxide anion (O2-), hydroxy radical (.OH), hydrogen peroxide and the like. It is known that excessive intake of the reactive oxygen species causes tissue damages in a human body and could lead to various kinds of disorders such as inflammation, aging, development of cancer and cardiac infarction. Especially, the hydroxy radical is most active among the reactive oxygen species, and it is considered that the hydroxy radical attacks the body in a diffusion-controlled manner and extracts hydrogen from fat in cells and the like. The fat is then changed into a peroxide lipid radical that causes the various disorders such as inflammation. Meanwhile, the body has a number of enzymes that reduces the reactive oxygen species. For example, superoxide dismutase (hereinafter called SOD) converts the superoxide anion into the hydrogen peroxide with a disproportionation reaction. Catalase and glutathione peroxidase vanish the superoxide anion.

Figure 4A:
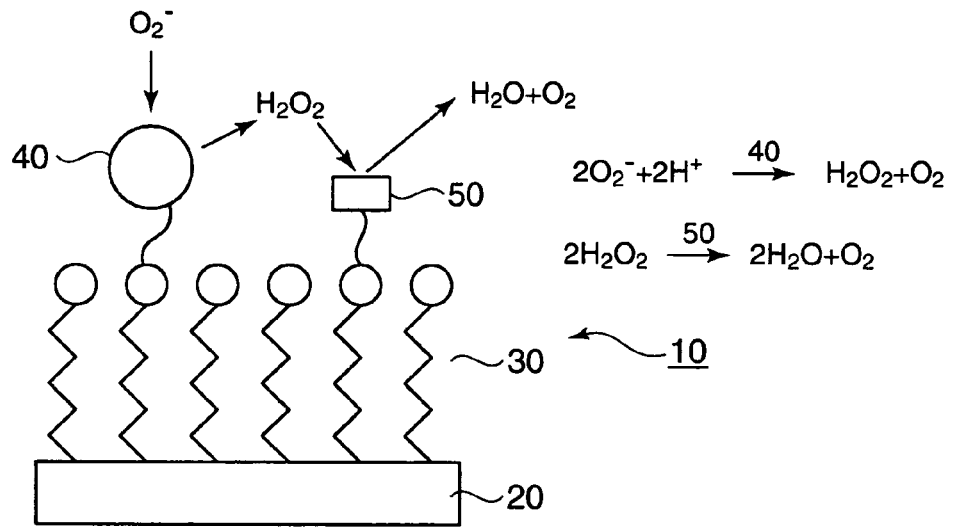
FIGS. 4A and 4B are schematic views showing a frame format of super oxide radical detection using the electrode substrate according to the embodiment of the invention.
Figure 4B:
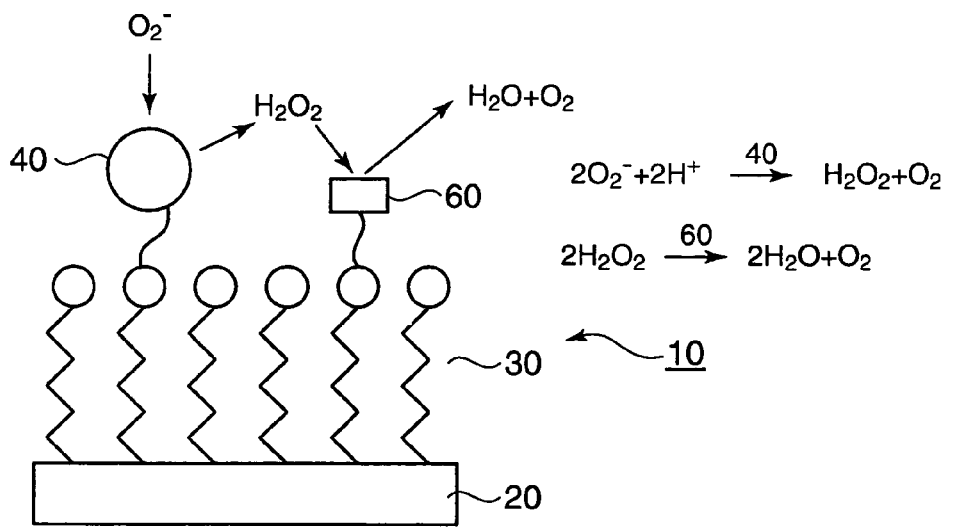

By using such phenomenon, it is possible to detect the superoxide radical as hereinafter described. FIGS. 4A and 4B are schematic views showing a frame format of the super oxide radical detection using the electrode substrate 10 according to the embodiment. FIG. 4A is a schematic view of the electrode substrate 10 modified with the combination of SOD 40 and catalase 50. FIG. 4B is a schematic view of the electrode substrate 10 modified with the combination of the SOD 40 and horseradish peroxidase 60. The modification of the electrode substrate 10 on which the membrane 30 is formed according to the embodiment can be performed with various enzymes through the hydroxyl group, a hydroxyl-induced maleimide group or the N-hydroxysuccinimide group that exist in the end of the membrane.

When the electrode substrate 10 on which the enzymes such as the SOD and the catalase 50 are immobilized is contacted with a sample solution containing the superoxide radical, the radical is firstly introduced into the reaction site of the SOD enzyme and then reduced to hydrogen peroxide by catalytic action of zinc, manganese or copper atom that exists in the reaction site as shown in FIG. 4A. The hydrogen peroxide is further reduced and transformed into water and oxygen by the catalase 50 that is immobilized on the electrode substrate as well as the SOD. At this point, the enzyme catalyze reaction is activated with the electrons supplied from the electrode substrate 10. Therefore, the amount of the reduction electrons supplied from the electrode substrate 10 can be measured as the reduction current. Accordingly, it is possible to decide the amount of the superoxide radical exiting in the sample by measuring the value of the reduction current. The measurement of the current can be carried out by the cyclic voltammetry, the differential pulse voltammetry and the like.

FIG. 4B is a schematic view of the superoxide radical detection by using the electrode substrate 10 which is modified with the horseradish peroxidase 60 (hereinafter called HRP) instead of the catalase 50 as shown in FIG. 4A. The reaction mechanism of the superoxide radical is same as that of the case using the catalase 50 as described above with reference to FIG. 4A.

According to the embodiments shown in FIG. 4A and FIG. 4B, the mediator that supports the electron transfer may be added. For example, ferrocene may be included.

Figure 5:
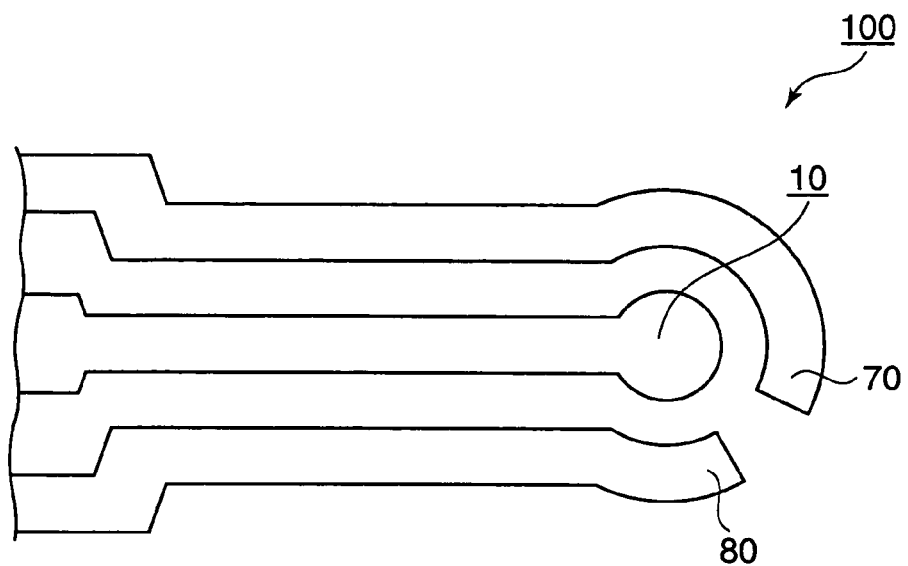
FIG. 5 is a schematic plan view of a detection device having the electrode substrate according to the embodiment of the invention, a counter electrode placed so as to oppose the electrode substrate and a reference electrode.

FIG. 5 is a schematic plan view of a detection device 100 having the electrode substrate 10 of the embodiment of the invention, a counter electrode 70 placed so as to oppose the electrode substrate 10 and a reference electrode 80. In FIG. 5, only main electrode components of the detection device 100 are shown. The counter electrode 70 used in the embodiment of the invention is not particularly limited. For example, the counter electrode 70 is made of platinum. The reference electrode 80 used in the embodiment is an electrode that provides a reference potential to the electric potential of the electrode substrate 10 and the counter electrode 70. Though it is not particularly limited, the reference electrode 80 is made of, for example, silver chloride. When the sample containing the subject material is provided in a form of droplet so as to cover the counter electrode 70, the reference electrode 80 and the electrode substrate 10 on which the enzyme and the like reacting with the subject material is immobilized, the electrons are given out and received on the electrode substrate 10. The detected current can be measured at a detection circuit 120 by electrically coupling the counter electrode 70, the reference electrode 80 and the electrode substrate 10 respectively to the detection circuit 120 though it is not shown in FIG. 5. The detection circuit 120 used in the embodiment of the invention is not particularly limited. For example, a thin film transistor is used. The measurement of the current can be carried out by an electrochemical measuring method such as the cyclic voltammetry and the differential pulse voltammetry.

A detection kit equipped with the detection device 100 is also provided according to an embodiment of the invention. More specifically, the detection kit according to the embodiment has the detection device 100, the biomolecule such as the enzyme that reacts with the subject material and the mediator that supports the transport of the electrons generated between the subject material and the biomolecule. The detection kit according to the embodiment can easily measure the glucose concentration and detect the reactive oxygen species contained in food as described above with reference to FIG. 3 and FIG. 4. The detection kit according to the embodiment further includes a buffer solution such as a phosphate buffer solution in order to control pH of the aqueous solution which is a reaction field. If the electrode substrate 10, the counter electrode 70, the reference electrode 80 and the detection circuit 120 according to the embodiment are made from thin film structures, the kit according to the embodiment can be minimized.

A method of detecting a subject material in a sample is also provided according to an embodiment of the invention. The detection method includes a step of preparing the above-described kit, and a step of contacting the sample containing the subject material such as a biologic sample, a food sample and an environmental sample including elements of water and air with the electrode substrate 10 in the above-mentioned kit. The presence or absence of the subject material can be determined by measuring the oxidation current or reduction current detected on the electrode substrate 10 by the cyclic voltammetry and the differential pulse voltammetry. In addition, if the standard curve of the subject material is provided in advance, it is possible to calculate the concentration of the subject material from the measurements of the oxidation current or reduction current with the above-described electrode substrate 10 both in the presence and absence of the subject material.

Figure 6:
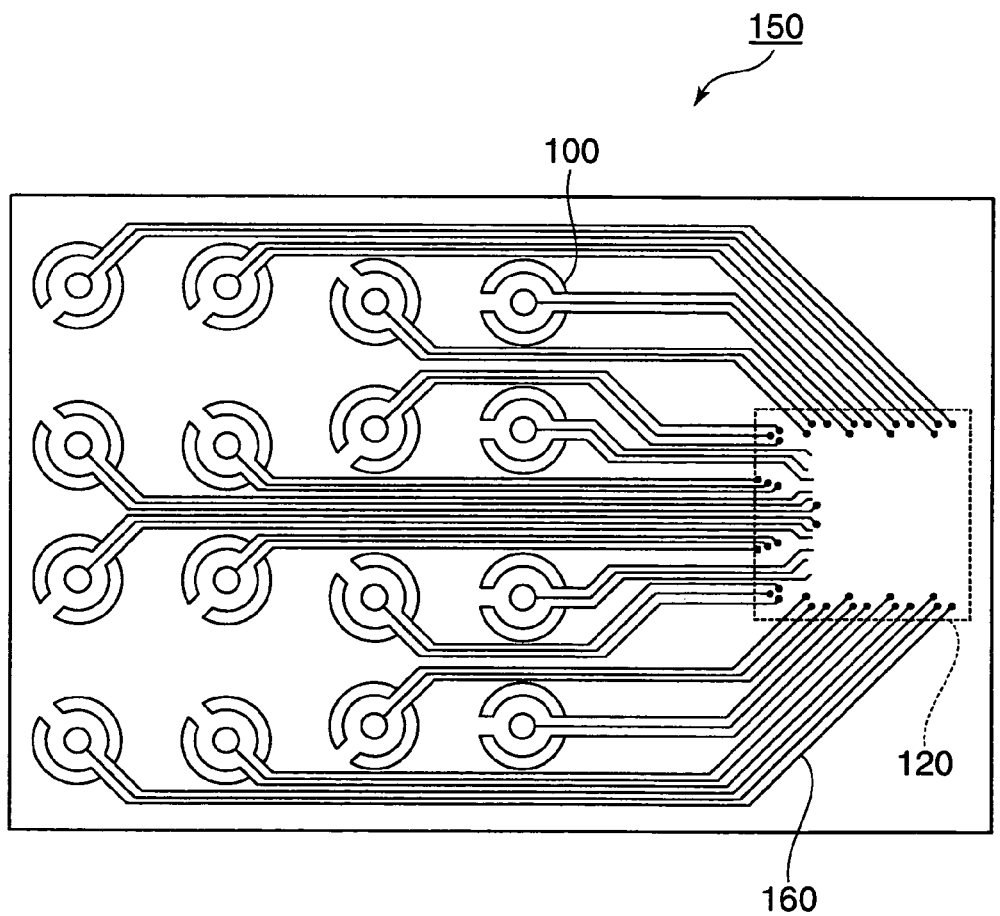
FIG. 6 is a schematic plan view of a device having a plurality of the detection devices according to the embodiment of the invention and detection circuits electrically coupled to the corresponding detection devices.

FIG. 6 is a schematic plan view of a device 150 having a plurality of the detection devices 100 according to the embodiment of the invention and a plurality of the detection circuits 120 electrically coupled to the corresponding detection devices. As for the electric connection between the detection circuit 120 and the detection device 100, the above-described electrode substrate 10, the counter electrode 70 and the reference electrode 80 are individually coupled to the detection circuit 120. If the detection circuit is made of a thin film transistor, it is possible to further amplify the detected current at the electrode substrate 10 by coupling the above-mentioned electrode substrate 10 to a drain of the thin film transistor.

This device can simultaneously carry out the detection of the subject material in a plurality of samples, which could be a single kind or different kinds, by contacting each detection device 100 with each sample as shown in FIG. 6. Furthermore, even in case of a single kind of the sample, samples with different concentrations can be provided to the detection devices 100 and detected by each of the detection devices 100. A circuit wiring that couples the detection device 100 and the detection circuit 120 is not particularly limited. For example, a silver wiring 160 and the like can be used to couple them.

Figure 7:
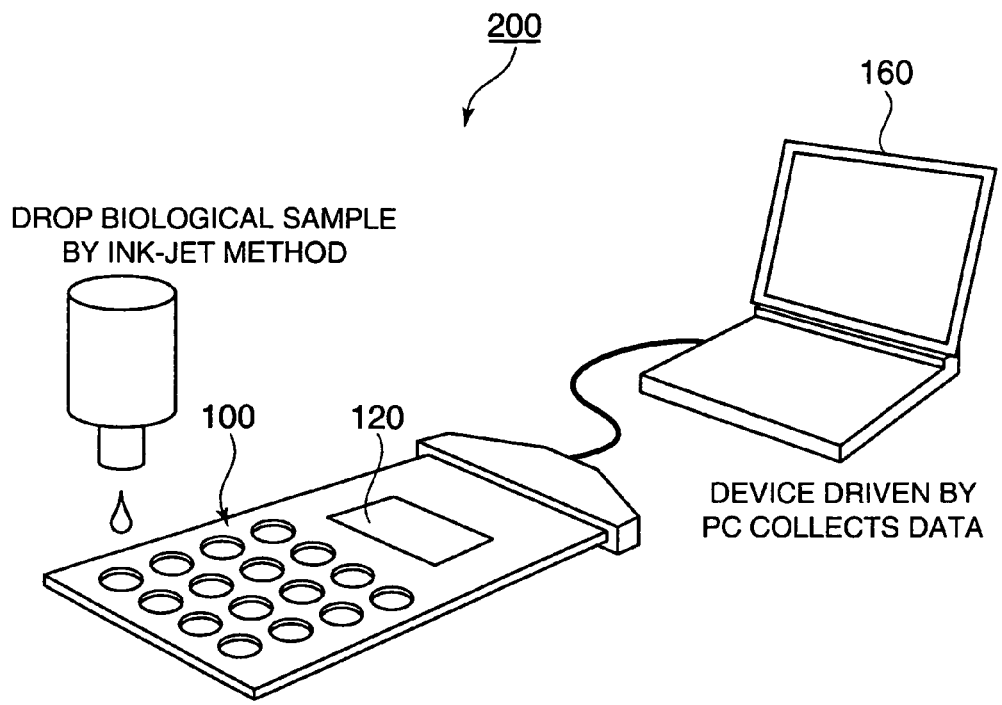
FIG. 7 is a schematic perspective view of a system in which the device shown in FIG. 6 is coupled to a personal computer and driven by the personal computer.

FIG. 7 is a schematic perspective view of a system 200 in which the device 150 shown in FIG. 6 is coupled to a personal computer 160 (hereinafter called PC) and driven by the PC. The device 150 in this embodiment is made disposable by covering the device with, for example, a plastic substrate. The plastic substrate used in the embodiment is not especially limited. For example, the substrate is made of acrylic resin, polycarbonate resin and the like. In this way, only the device 150 is made disposable and the device can be easily used for the management of the blood sugar level, the detection of the reactive oxygen species contained in food and the like. Since the device 150 is coupled to the PC, information obtained by the thin film transistor which is the detection circuit 120 can be set to the PC through an interface such as universal serial bus (USB). Accordingly, the detection can be driven by the PC. Furthermore, if a radio frequency (RF) tag coupled to the thin film transistor is provided in the device 150, the information obtained by the thin film transistor can be wirelessly transmitted to the PC. When the detection of the sample is carried out, the droplet of the sample may be provided by a microspotting method, an inkjet method and the like. The detection is performed when the droplet of the sample contacts with the electrode substrate 100 according to the embodiment of the invention. With such system 200, it is possible to provide the sensor system 200 that can perform the detection in vitro and in real time.

The foregoing description has been given by way of example only and it will be appreciated by a person skilled in the art that modifications can be made without departing from the scope of the invention. Such modification will be included in the invention defined by the claims laid out herein.

PRACTICAL EXAMPLE 1

Figure 8:
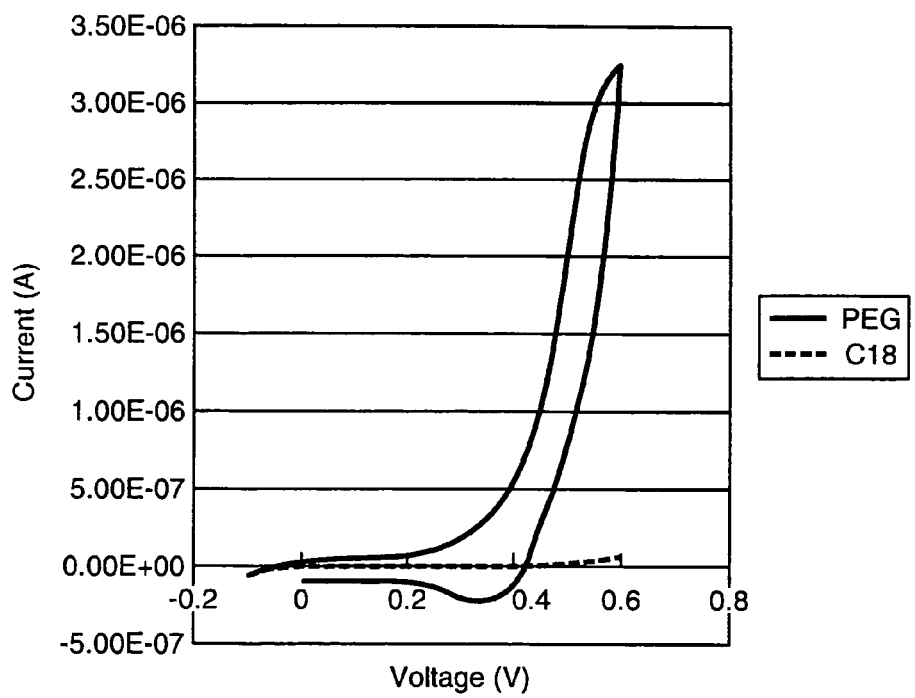
FIG. 8 shows a result of cyclic voltammetry obtained in glucose detection using the electrode substrate.

An enzyme reaction is induced when the glucose is added to the glucose oxidase solution, producing gluconic acid. At this point, the oxidation current is produced. How much the produced oxidation current is selectively transmitted was measured by the cyclic voltammetry (CV) with the electrode having a membrane made of thiol including polyethylene glycol (PEG) and with the electrode having a membrane made of alkane thiol. 0.1 M of the glucose oxidase enzyme molecule is dispersed in a phosphate buffered saline (PBS) solution in the concentration of 1.2 mg/100 ml. 0.1 M of Fe$(CN)_6^{3-}$ is further mixed and the solution is sufficiently substituted by nitrogen. A sample electrode substrate (working electrode) which is a gold electrode modified with the membrane, a Pt counter electrode and a AgCl reference electrode are put in the solution at 35° C. and the CV measurements were carried out after the glucose is added (see FIG. 8). The oxidation current was not detected with the thick membrane made of C18 (hexadecane thiol) (corresponds to C18 in FIG. 8) among the membranes made of the alkane thiol because the membrane served as an insulating film on the electrode surface.

On the other hand, the membrane made of C6 (hexane thiol) easily transmits the oxidation current since it is a thin membrane (about 5 Å thick). However, this could be problem in terms of selectivity because the current produced by other factors than the enzyme reaction is also detected. It is turned out that the membrane including the PEG can selectively and effectively transport the oxidation current produced by the enzyme reaction (corresponds to PEG in FIG. 8) even though the thickness of the membrane is about 25 Å. When the glucose was not added under the presence of the glucose oxidase and the voltage was kept applied to the electrode, the current was not detected at all at the electrode surface on which the membrane including the highly-electron transmissive PEG was formed because the enzyme reaction did not occur. This demonstrates that the PEG membrane transports only the reaction electrons that are produced from the enzyme reaction toward the electrode.

PRACTICAL EXAMPLE 2

The electrode substrate using the SOD and the HRP as the enzyme was formed according to the embodiment in order to detect the superoxide radical. A way to immobilize the enzyme molecules to the electrode substrate is not especially limited. For example, it may be carried out as follows. 10 mM of aminoethanethiol is mixed into a dimethylsulfoxide solution and a gold electrode substrate is immersed in the solution for two hours. Then, the SAM whose surface is covered with the amino groups is formed. Next, the amino coating electrode substrate is immersed in a 1% glutaraldehyde solution, the gold electrode substrate with an aldehyde coating surface is formed. The substrate is again immersed in a 50 mM PBS solution in which 50 units/ml of the SOD is dispersed. In this way, the imide bindings are formed by reacting the amino group on the enzyme surface with the aldehyde group. In this way, the enzyme is immobilized. The other enzyme HRP is also immobilized to the electrode substrate surface in the same way as described above. When a sample solution containing the superoxide radical contacts with the electrode substrate on which the immobilized enzyme molecule film is formed, the radical is reduced to the hydrogen peroxide by the action of enzyme SOR. The hydrogen peroxide is further reduced by the HRP immobilized on the electrode surface in the same way as the SOD and the water and the oxygen are produced. At this point, the enzyme catalyze reaction is activated with the electrons supplied from the electrode substrate. Therefore, the amount of the reduction electrons supplied from the electrode can be measured by the cyclic voltammetry as the reduction current. If the amount of the reduction current is large, the sample solution contains a large amount of the superoxide radical species. On the contrary, if the amount of the reduction current is small, there is a small amount of the superoxide radical in the sample solution.

Advantageous Effect of the Invention

According to the above-described electrode substrate, the biomolecule and the like will not adhere to the surface of the electrode substrate and the electrons can be selectively transported through the electrode. Moreover, it is possible to provide the detection kit that can easily detect a subject material by using the electrode substrate. Furthermore, it is possible to provide the detection kit and the detection method for detecting the subject material such as the glucose and the superoxide radical when the above-described detection device, the biomolecule and the mediator are combined.

What is claimed is:

1. An electrode substrate, comprising:
    an electrode;
    a membrane disposed on the electrode;
    a mediator; and
    a glucose oxidase,
    the membrane having a monolayer including a chemical compound having a group represented by a following formula (1)

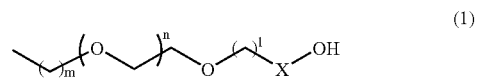

the m, the n, and the l being positive integers more than 0, and the X indicating a methylene group or a carbonyl group,
the membrane having a first end and a second end,
the mediator and the glucose oxidase combining to a first functional group existing at the first end of the membrane, and
the second end combining to the electrode.

2. The electrode substrate according to claim 1, a thickness of the membrane being 10-80 Å, a carrier being exchanged between the electrode and the membrane.

3. The electrode substrate according to claim 1, wherein the electrode and the membrane are bonded through a sulfur atom or an oxygen atom.

4. A detection device, comprising:
    the electrode substrate according to claim 1;
    a counter electrode opposing the electrode substrate; and
    a reference electrode.

5. The detection device according to claim 4, further comprising:
    a detection circuit individually coupled to the electrode substrate, the counter electrode and the reference electrode.

6. A detection kit for detecting a subject material, comprising:
    the detection device according to claim 4; and
    a biomolecule or a mediator reacting with the subject material.

7. The detection kit according to claim 6, further comprising a buffer solution.

8. A method of detecting a subject material in a sample, comprising:
    providing the detection kit according to claim 6; and
    contacting the sample with the kit.

9. The method of detecting a subject material in a sample according to claim 8, further comprising:
    measuring a current value in the presence of the subject material.

10. The electrode substrate according to claim 1, the mediator including a ferocene or ferocene derivative.

11. The electrode substrate according to claim 1, further comprising:
    a reaction coenzyme that is a pyroquinoline quinine or a nicotinamide adenine dinucleotide.

12. The electrode substrate according to claim 1, wherein a flavin adenine dinucleotide is at an active center of the glucose oxidase.

* * * * *